US00PP15958P2

(12) United States Plant Patent
Van Andel

(10) Patent No.: US PP15,958 P2
(45) Date of Patent: Sep. 13, 2005

(54) *NEPHROLEPIS* PLANT NAMED 'NR. 20'

(50) Latin Name: *Nephrolepis exaltata*
Varietal Denomination: Nr. 20

(75) Inventor: Otto Jan Robert Van Andel, De Kwakel (NL)

(73) Assignee: Braam Young Plants B.V., De Kwakel (NL)

( * ) Notice: Subject to any disclaimer, the term of this patent is extended or adjusted under 35 U.S.C. 154(b) by 42 days.

(21) Appl. No.: 10/837,786

(22) Filed: May 3, 2004

(51) Int. Cl.[7] ..... A01H 7/00
(52) U.S. Cl. ..... Plt./379
(58) Field of Search ..... Plt./379

(56) References Cited

U.S. PATENT DOCUMENTS

PP14,995 P2 * 7/2004 Van Andel ..... Plt./379

OTHER PUBLICATIONS

UPOV ROM GTITM Computer Database, GTI JOUVE Retrieval Software 2004/04 citation for 'Nr. 20'.*

* cited by examiner

*Primary Examiner*—Anne Marie Grunberg
*Assistant Examiner*—W. C. Haas
(74) *Attorney, Agent, or Firm*—C. A. Whealy

(57) ABSTRACT

A new and distinct cultivar of *Nephrolepis* plant named 'Nr. 20', characterized by its mostly upright and somewhat outwardly arching plant habit; strong, erect and visible rachis; and uniquely-shaped undulate pinnae.

1 Drawing Sheet

Botanical designation: *Nephrolepis exaltata.*
Variety denomination: 'Nr. 20'.

BACKGROUND OF THE INVENTION

The present invention relates to a new and distinct cultivar of *Nephrolepis* fern plant, botanically known as *Nephrolepis exaltata,* and hereinafter referred to by the name 'Nr. 20'.

The new *Nephrolepis* fern is a naturally-occurring whole plant mutation of the *Nephrolepis exaltata* cultivar Nr. 21, (U.S. Plant Pat. No. 14,995). The new *Nephrolepis* fern was discovered by the Inventor in a controlled environment in De Kwakel, The Netherlands in November, 2001, as a single plant within a population of plants of the cultivar Nr. 21.

Since May, 2002, asexual reproduction by divisions of the new *Nephrolepis* fern in a controlled environment at De Kwakel, The Netherlands has shown that the unique features of this new *Nephrolepis* fern are stable and retained through successive generations of asexual reproduction.

SUMMARY OF THE INVENTION

The new *Nephrolepis* fern has not been observed under all possible environmental conditions. The phenotype may vary somewhat with variations in environment such as temperature and light intensity without, however, any variance in genotype. The following observations, measurements and comparisons describe plants grown in De Kwakel, The Netherlands, under conditions generally used in commercial practice.

The following traits have been repeatedly observed and are determined to be the unique characteristics of 'Nr. 20'. These characteristics in combination distinguish 'Nr. 20' as a new and distinct cultivar of *Nephrolepis:*

1. Mostly upright and somewhat outwardly arching plant habit.
2. Strong, erect and visible rachis.
3. Uniquely-shaped undulate pinnae.

The new *Nephrolepis* fern is most similar to its parent cultivar, the *Nephrolepis exaltata* cultivar Nr. 21. However in side-by-side comparisons conducted in De Kwakel, The Netherlands, the new *Nephrolepis* fern differed from plants of the cultivar Nr. 21 in the following characteristics:

1. Plants of the new *Nephrolepis* fern were larger than plants of the cultivar Nr. 21.
2. Plants of the new *Nephrolepis* fern had longer and wider fronds than plants of the cultivar Nr. 21.
3. Plants of the new *Nephrolepis* fern and the cultivar Nr. 21 differed in pinnae shape.

The new *Nephrolepis* fern can be compared to plants of the *Nephrolepis exaltata* cultivar Corditas, not patented. However in side-by-side comparisons conducted in De Kwakel, The Netherlands, the new *Nephrolepis* fern differed from plants of the cultivar Corditas in the following characteristics:

1. Plants of the new *Nephrolepis* fern had longer, stiffer and more upright fronds than plants of the cultivar Corditas.
2. Plants of the new *Nephrolepis* fern and the cultivar Corditas differed in pinnae shape.
3. Rachis of plants of the new *Nephrolepis* were more visible than rachis of plants of the cultivar Corditas.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Nephrolepis* fern.

The photograph at the top of the first sheet comprises a side perspective view of a typical plant of 'Nr. 20'.

The photograph at the bottom of the sheet comprises a close-up view of typical fronds of 'Nr. 20' (left) and 'Nr. 21' (right).

DETAILED BOTANICAL DESCRIPTION

Plants in the aforementioned photographs and used in the following description were grown under conditions which closely approximate commercial production conditions from February to June in a glass-covered greenhouse in De Kwakel, The Netherlands. During the production of the plants, day temperatures were about 22° C., night temperatures were about 19° C. and light levels were about 22,000 to 28,000 lux. Plants in the photographs and used for the description were about six months old when the photographs and description were taken.

Botanical classification: *Nephrolepis exaltata* cultivar Nr. 20.

Parentage: Naturally-occurring whole plant mutation of *Nephrolepis exaltata* cultivar Nr. 21 (U.S. Plant Pat. No. 14,995).

Propagation: By tissue culture.

Propagation:

*Time to initiate roots, summer.*—About 30 days at 24° C.

*Time to initiate roots, winter.*—About 35 days at 22° C.

*Root description.*—Fine and brown in color.

Plant description:

*Growth habit.*—Mostly upright and somewhat outwardly arching; symmetrical; appropriate for 10 to 15-cm containers.

*Plant height.*—About 50 to 60 cm from soil line to top of plant plane.

*Plant width.*—About 100 cm.

*Plant vigor.*—Moderate.

*Frond description.*—Quantity of fronds per plant: About 100. Leaf arrangement: Bi-pinnate. Frond length: About 30 to 60 cm. Frond width: About 4 to 11 cm. Rachis length: About 30 to 60 cm. Rachis diameter: About 1.5 to 2.5 mm. Rachis color: Between 146A and 148A; towards the base, overlain with 187A.

*Pinnae description.*—Shape: Roughly deltoid, elongate, narrow. Length: About 2 to 4 cm. Width: About 1 to 1.5 cm. Quantity of pinnae: About 60 to 80 per frond. Margin: Towards the apex, deeply dissected and slightly crenate; towards the base, entire; feathery. Apex: Acute. Base: Truncate, asymmetrical. Aspect: Undulate along axis. Attachment: Sessile. Texture, upper and lower surfaces: Leathery; glabrous. Venation pattern: Pinnate. Color: When developing, upper surface: Towards the base, 137A; towards the apex, 144B. When developing, lower surface: Towards the base, 137B; towards the apex, 144A. Fully developed, upper surface: Towards the base, 137A; towards the apex, between 143A and 137A. Fully developed, lower surface: Towards the base, 137A; towards the apex, 144A. Venation, upper surface: Similar to lamina. Venation, lower surface: Main vein, 187A; lateral veins, 146B.

*Spores.*—None observed.

Disease/pest resistance: Resistance to pathogens and pests common to *Nephrolepis* ferns has not been observed.

Temperature tolerance: Plants of the new *Nephrolepis* fern have been observed to be tolerant to temperatures ranging from 12 to 32° C.

It is claimed:

1. A new and distinct cultivar of *Nephrolepis* plant named 'Nr. 20', as illustrated and described.

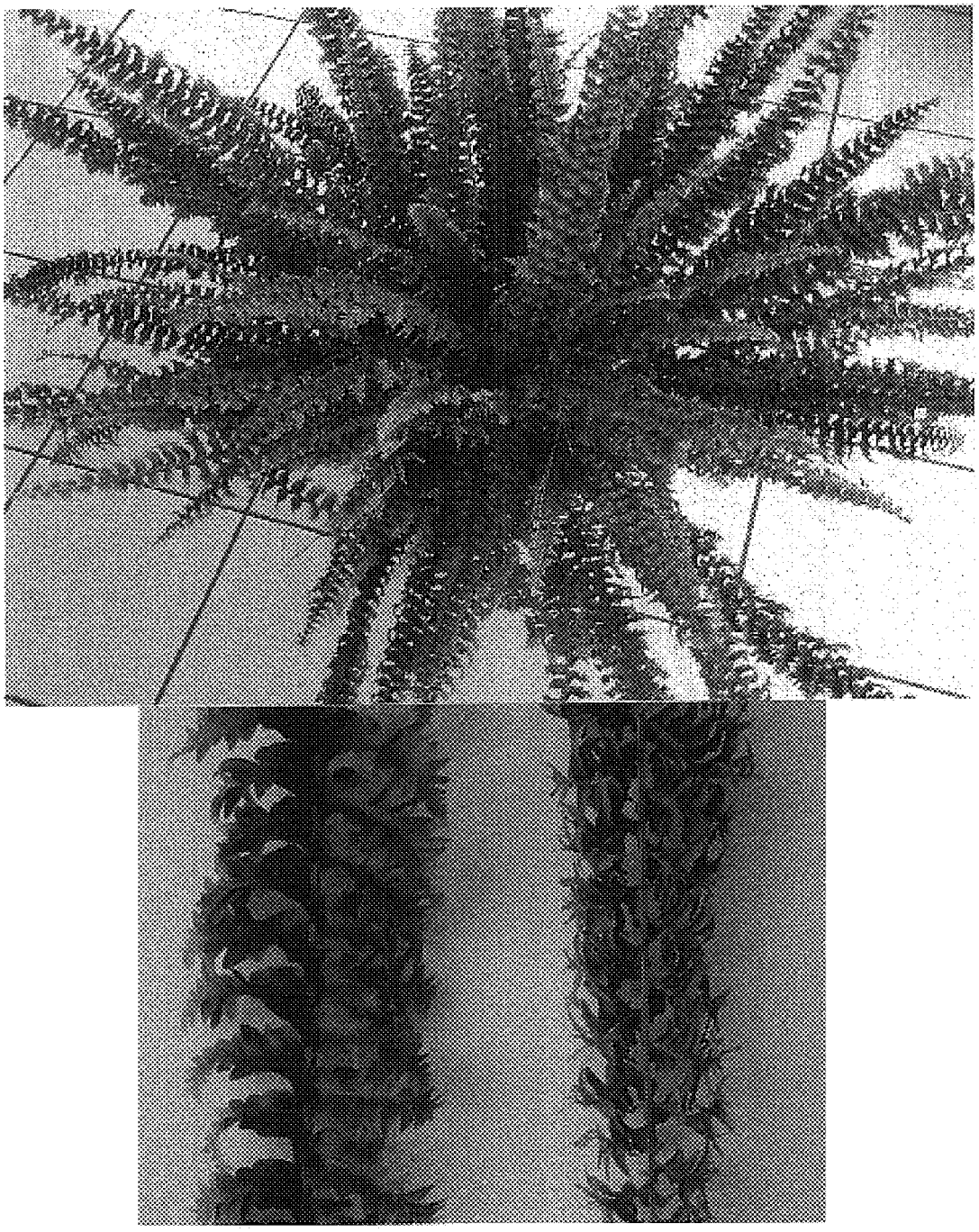

* * * * *